(12) United States Patent
Del Deo et al.

(10) Patent No.: US 9,808,322 B2
(45) Date of Patent: Nov. 7, 2017

(54) METHOD AND DEVICE FOR POSITIONING AND STABILIZATION OF BONY STRUCTURES DURING MAXILLOFACIAL SURGERY

(71) Applicants: Vito Del Deo, Forio (IT); Xinsheng Cedric Yu, Pasadena, MD (US)

(72) Inventors: Vito Del Deo, Forio (IT); Xinsheng Cedric Yu, Pasadena, MD (US)

( * ) Notice: Subject to any disclaimer, the term of this patent is extended or adjusted under 35 U.S.C. 154(b) by 0 days.

(21) Appl. No.: 14/838,065

(22) Filed: Aug. 27, 2015

(65) Prior Publication Data
US 2016/0183979 A1  Jun. 30, 2016

Related U.S. Application Data

(60) Provisional application No. 62/042,500, filed on Aug. 27, 2014.

(51) Int. Cl.
| | | |
|---|---|---|
| A61B 17/00 | (2006.01) | |
| A61B 90/14 | (2016.01) | |
| A61B 34/10 | (2016.01) | |
| A61B 17/80 | (2006.01) | |
| A61B 90/57 | (2016.01) | |
| A61B 90/16 | (2016.01) | |
| A61B 90/50 | (2016.01) | |

(52) U.S. Cl.
CPC .......... *A61B 90/14* (2016.02); *A61B 17/8085* (2013.01); *A61B 34/10* (2016.02); *A61B 90/16* (2016.02); *A61B 90/57* (2016.02); *A61B 2034/107* (2016.02); *A61B 2090/508* (2016.02)

(58) Field of Classification Search
CPC ................................ A61B 90/14; A61B 90/57
USPC ....................................................... 606/54–59
See application file for complete search history.

(56) References Cited

U.S. PATENT DOCUMENTS

| | | | | |
|---|---|---|---|---|
| 4,510,926 A | * | 4/1985 | Inaba ..................... | A61B 90/50 600/231 |
| 5,300,080 A | * | 4/1994 | Clayman ................ | A61B 90/11 604/117 |
| 5,330,485 A | * | 7/1994 | Clayman ................ | A61B 90/11 606/1 |
| 7,404,792 B2 | * | 7/2008 | Spence .................. | A61B 17/02 600/37 |

(Continued)

OTHER PUBLICATIONS

Leksell, L., Cerebral Radiosurgery. I. Gammathalmotomy in Two Cases of Intractable Pain, Acta chirurgica Scandinavica, vol. 134, p. 585-595; 31 (1968).

*Primary Examiner* — Ellen C Hammond
*Assistant Examiner* — Stuart S Bray
(74) *Attorney, Agent, or Firm* — Baker Donelson, PC; Royal W. Craig (57) ABSTRACT

A maxillofacial or cranial-facial surgical stabilizer comprising a head frame fully or partially surrounding the head of a patient at an angle running from ears to temple, and that is fixated to the skull of the patient by multiple screws and/or ear holders and screws. One or more flexible/locking arms are removably attached to the head frame for holding and positioning a plurality of interchangeable instruments or accessories. One flexible/locking arm is a medial/center arm accessorized with a dental arch mold. A method of using a head frame to position the pieces of bones during maxillofacial or cranio-facial surgery is also provided.

15 Claims, 8 Drawing Sheets

(56) References Cited

U.S. PATENT DOCUMENTS

| | | | | |
|---|---|---|---|---|
| 7,730,563 B1* | 6/2010 | Sklar | | A61G 13/121 5/622 |
| 7,792,341 B2* | 9/2010 | Schutyser | | G06T 7/0012 382/128 |
| 7,925,328 B2* | 4/2011 | Urquhart | | A61B 90/14 600/429 |
| 8,240,967 B2* | 8/2012 | Guglielmelli | | A47G 21/08 414/9 |
| 8,287,537 B2* | 10/2012 | Dinkler, II | | A61B 17/6433 606/56 |
| 8,646,452 B2* | 2/2014 | Sklar | | A61G 13/121 128/845 |
| 8,844,536 B1* | 9/2014 | Schuele | | F16B 2/12 128/845 |
| 9,216,126 B2* | 12/2015 | Schuele | | A61G 13/121 |
| 9,402,692 B2* | 8/2016 | Schuele | | A61B 90/57 |
| 2001/0029379 A1* | 10/2001 | Grotehuis | | A61B 90/14 606/130 |
| 2006/0025730 A1* | 2/2006 | Hartigan, Jr. | | A45D 29/00 604/322 |
| 2006/0129126 A1* | 6/2006 | Kaplitt | | A61M 25/00 604/513 |
| 2006/0150984 A1* | 7/2006 | Ferguson | | A61F 5/3707 128/846 |
| 2007/0106169 A1* | 5/2007 | Fadem | | A61B 5/04845 600/544 |
| 2009/0211026 A1* | 8/2009 | Schoff | | A61G 1/04 5/600 |
| 2009/0264938 A1* | 10/2009 | Bailey | | A61B 90/14 606/329 |
| 2010/0152749 A1* | 6/2010 | von Pechmann | | A61B 90/50 606/130 |
| 2010/0268248 A1* | 10/2010 | Hong | | A61B 19/203 606/130 |
| 2011/0160727 A1* | 6/2011 | Arn | | A61B 90/14 606/59 |
| 2011/0200977 A1* | 8/2011 | Paronen | | G09B 23/30 434/268 |
| 2014/0066931 A1* | 3/2014 | Myers | | A61B 17/6458 606/59 |
| 2014/0194740 A1* | 7/2014 | Stein | | A61B 8/085 600/455 |
| 2015/0297176 A1* | 10/2015 | Rincker | | A61B 8/0808 600/439 |
| 2016/0183979 A1* | 6/2016 | Del Deo | | A61B 17/8085 606/56 |
| 2016/0346930 A1* | 12/2016 | Hares | | B25J 9/1679 |
| 2016/0361133 A1* | 12/2016 | Davis | | A61B 17/3211 |

\* cited by examiner

METHOD AND DEVICE FOR POSITIONING AND STABILIZATION OF BONY STRUCTURES DURING MAXILLOFACIAL SURGERY

CROSS-REFERENCE TO RELATED APPLICATION(S)

The present application derives priority from U.S. provisional application Ser. No. 62/042,500 filed Aug. 27, 2014.

BACKGROUND OF THE INVENTION (1) Field of the Invention

The present invention relates to maxillofacial surgery. Specifically, it relates to stabilizers for positioning and stabilizing fractured or surgically mobilized bony structures and, more specifically, to a stabilizer for bony structures such as the midface/maxillae and mandible for use in maxillofacial surgical procedures.

(2) Description of Prior Art

Facial and mandibular bones may be broken up for surgical purpose or accidentally in a traumatic injury. There are a variety of cranio-facial procedures available for trauma and malformation in which the broken bones are re-connected together to achieve both function and cosmetic results. Currently, these procedures are performed by surgeons and one or more surgical assistants. The surgeon will manually position the bone to the best possible alignment, and the broken pieces are then connected using metal plates and screws. The conventional approach to positioning, orienting, and stabilizing the unstable or mobile bone segments is completely by hand, with minimal or no instrument assistance. The examples of instrumental assistance including splits made with dental castings. Such manual manipulation for finding the best fit of the segments often requires several consecutive maneuvers in a repetitive pattern, and can be challenging for the surgeon. At the very least it diverts the surgeon's concentration, efforts and time away from the procedure itself. This loss of focus can result in suboptimal results, such as limited movement and facial dimensional imbalance and/or asymmetry.

To aid the manual orientation, positioning and fixation process, surgical planning systems were proposed. For example, U.S. Pat. No. 7,792,341 to Filip Schutyser proposes a surgical planning system that uses three-dimensional images of the patient to create three-dimensional surfaces of structures in the maxillofacial region and generate two-dimensional images (cephalograms). Such image manipulation allows the analyses and planning of the maxillofacial surgical procedures. The output from such maxillofacial surgery planning system can be the parameters for making plaster molds, making surgical splints, or to a computer display that simulates the procedure as a means of navigating the surgeon through the manipulation process (see, e.g., FIG. 13 and FIG. 15 of U.S. Pat. No. 7,792,341). Although such planning is useful in making the necessary molds and splints to aid the procedure, it does not help in the actual manipulation process. It also does not provide the guidance for fine tuning and adjustment before fixation.

Ideally, the positional accuracy and the match to the original geometry (in the case of a trauma) or the newly obtained facial symmetry (in the case of a malformative syndrome) should be established by standard anthropometric analysis using precise anthropometric measuring tools, and then verified radiologically prior to fixation with plates and screws. However, this is not possible when the bone pieces are being held together by hand. Similarly, surgical residents cannot learn the skills if they cannot see the surgery because the surgeon is hovering over the patient.

What is needed is a stabilizer device to make the procedure less operator dependent, to allow objective verification of the bone positioning and fine adjustment prior to fixation, and to allow trainees in the room to view the positioning and orientations of all bone pieces before they are screwed together.

Figures 1, 2, 3:
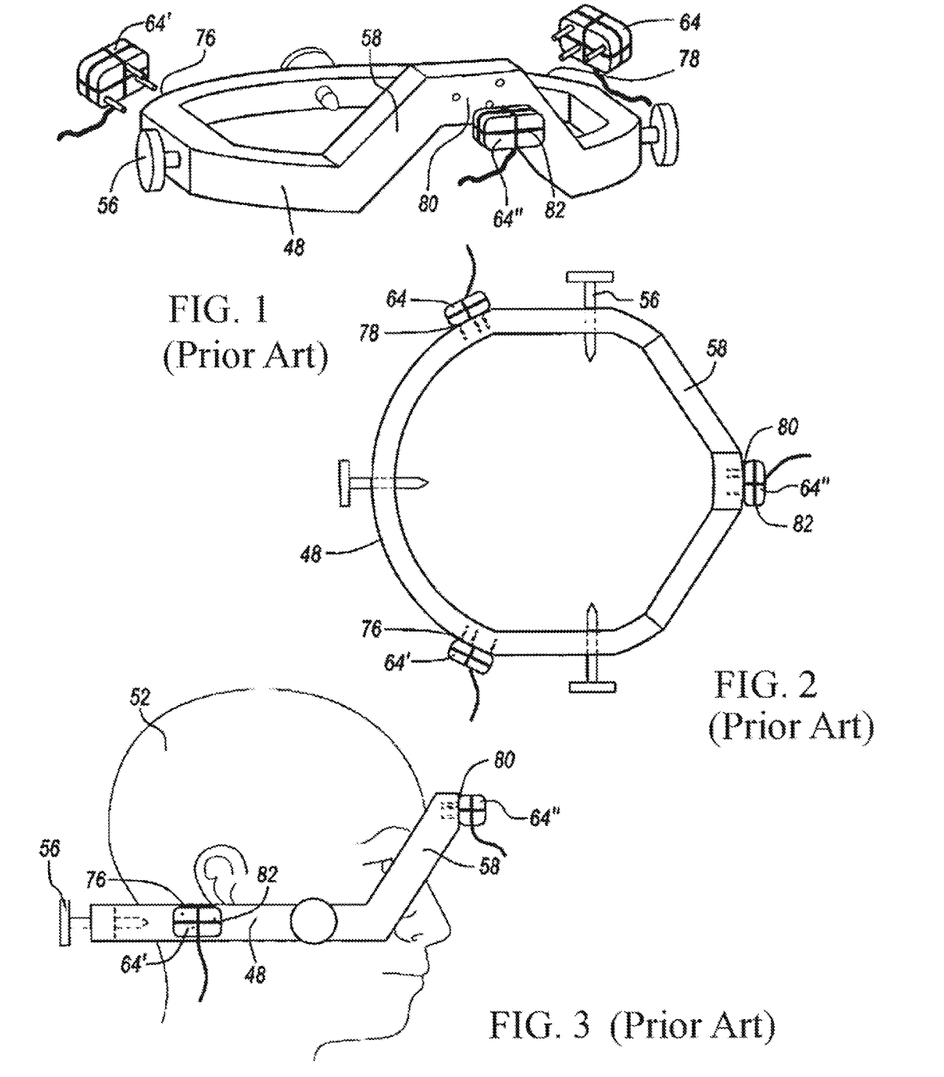
FIG. 1 is a front perspective view of a prior art head frame attached to a patient's skull.
FIG. 2 is a top view of the prior art head frame of FIG. 1.
FIG. 3 is a side view of the prior art head frame of FIGS. 1-2.

Headframes for stereotactic neurosurgery and radiosurgery are well known. These headframes are ring-shaped structures which are mounted to the skull of a patient to provide a fixed reference with respect to the patient's skull. A typical stereotactic head frame is a halo affixed to a patient's skull (under anesthesia) using pins or screws. The stereotactic frame may also act as a guide for delivering various instruments such as a biopsy needle or DBS leads or electrodes. FIGS. 1-3 are a front perspective view, top view, and side view, respectively, of a prior art head frame as shown in U.S. Pat. No. 7,925,328 to Urquhart et al. issued Apr. 12, 2011. The frame 1 is attached to a patient's skull with three screws 2 fixed into the frontal outer cortical bone/outer layer. Such devices offer accurate neurosurgical localization during procedures such as stereotactic cranial biopsy and cranial surgery. For example, for radiosurgery of intracranial lesions, a head frame is used to localize the lesion and to position the lesion at the center of the radiation focus. See, Leksell, L., "Cerebral Radiosurgery. I. Gammathalmotomy In Two Cases Of Intractable Pain", Acta chirurgica Scandinavica, vol. 134, p. 585-595; 31 (1968). However, such head frames have not been suggested or used for aiding maxillofacial or cranio-facial surgery. A common drawback of the frames disclosed by Urquhart et al and Leksell is that these frames cannot be adjusted to the head size and shape and they interfere with the maxillofacial surgeon's work.

During maxillofacial trauma procedures and orthognathic/malformative procedures, the positioning, orienting and stabilizing (POS) of unstable/mobile bony segments are performed manually by surgeons without instrumental aids. Such maneuvers are often tiresome and time consuming. Human hands often lack long-term consistency, stability and strength, and so clinical results are often operator dependent. Other drawbacks of the current practice include the infeasibility of position verification before fixation, and the limited teaching/education capacity. These are all factors that can interfere, affecting that final position of the skeletal segment and leading to undesired results, such as asymmetry and suboptimal chewing function.

In view of the foregoing, the present disclosure provides a method and device for positioning and stabilization of bony structures during maxillofacial surgery that improves clinical performance of surgeons by freeing the surgeon's hands so that two-dimensional or three dimensional radiological images can be taken and verified against prior image sets and/or reference data. It is also the objective of the present disclosure to allow very fine adjustments to a stabilized arrangement of bony segments if desired prior to bone fixation. The device frees the surgeon's hands and makes their task less strenuous, more accurate, easier and efficient. The device is specifically configured to stabilize the mandible and/or the upper pallet for the purpose of maxillofacial and cranio-facial surgery without interfering with the procedure or anesthesia equipment.

SUMMARY OF THE INVENTION

Accordingly, it is an object of the present invention to provide a maxillofacial surgical stabilizer capable of holding a plurality of instruments in any desired position about the head, and which allows repositioning of the instrument(s) quickly and easily by single-handed manipulation.

It is another object to provide a maxillofacial surgical stabilizer as above that provides full multidirectional adjustability of the location of the desired instrument.

It is still another object to provide a maxillofacial surgical stabilizer with the adjustability as above and yet which can be selectively locked into position for rigid, reliable and secure support of an instrument or instruments.

In accordance with the foregoing and other objects, the present invention is a maxillofacial or cranial-facial surgical stabilizer. The device comprises a metal frame that is fixated to the skull of the patient with multiple screws, or a combination of external ear holders and screws. On the frame, a plurality (minimum one-maximum five) of flexible arms can be optionally attached and interchangeably accessorized. These flexible arms can each be stiffened by a tightening lever. At the free ends of the arms, accessories such as dental molds, clamps and retractors can be attached in a fashion as a surgical set-up splint that can be used to replicate the planned position and also to support, orient and stabilize the maxillae/upper jaw in relation to the skull. The accuracy of the bony segments positioned and stabilized according to the procedures and with the stabilizer disclosed above can now be verified radiographically.

It is also the objective of the present disclosure to provide a computer system to aid the anthropometric analysis. The computer system is referred to as the anthropometric planning system (APS). The radiographs can be manipulated and compared with prior radiographs in the APS. The mandible can be rotated on the APS screen to reveal any gaps or obstructions. The matching of the upper and lower teeth can also be verified. The positions of all bony segments can be fine-tuned virtually on the APS to reach their ideal position. The required translations and rotations of each of the arms to reach these ideal settings are calculated and displayed and/or printed.

The APS of the present invention is specifically designed for use in combination with the stabilizer of the invention. Specifically, the APS is dedicated to the fine tuning of the fixation arms of the present disclosure rather than planning the molds or a splint as with prior art maxillofacial surgery planning systems. Alternately, the APS may be used to provide a virtual simulation of a procedure to navigate a manual procedure. Without the stabilizer and the ability to make fine adjustments, the plan, no matter how good, cannot be executed accurately. This way, the output of the plan is not simply virtual images on a screen showing how to put the bony segments together, but guided instructions explaining to the operator which knob on which joint the stabilizer arms is connected to turn, and by how many degrees, so that the bony segments are perfectly aligned. The planning process is also different: rather than operating on the bones, the present planning system operates on the freedom offered by the adjustable base joints.

To facilitate the required fine adjustments, the joint of the flexible arm and the metal frame contains mechanisms to allow the attached arm to make fine translational adjustments in all three dimensions and to make fine rotational adjustments about one or more axes. The availability and ranges of all forms of adjustments are known to the APS so that the APS will only make executable adjustments.

In view of the above, a method of using a head frame and mechanical arms mounted on it to position the pieces of bones during maxillofacial or cranio-facial surgery is also provided. The method comprises i) attaching a head frame bearing one or more mechanically-positionable arms to the skull of the patient; ii) using a dental mold and/or other instruments (clamps, retractors, etc.) held in the arms mounted on the metal frame to position, orient and secure the upper jaw and additional bony pieces in their optimal positions; iii) make further fine adjustment of the stiffened arrangement by adjusting a joint positioning mechanism; iv) verifying the correct positioning and orientation radiologically; v) optionally, using the APS to make virtual verification and adjustments to yield the required fine adjustments; vi) make the fine adjustments required by the APS on the joint positioning mechanism; and repeat steps iv) to vi) is necessary; and vii) fixating the pieces with metal fixation parts.

BRIEF DESCRIPTION OF THE DRAWINGS

Other objects, features, and advantages of the present invention will become more apparent from the following detailed description of the preferred embodiments and certain modifications thereof when taken together with the accompanying drawings in which:

FIG. 4a is a front perspective view of a maxillofacial surgical stabilizer 2 according to the present invention.

FIG. 4b is a top view of the maxillofacial surgical stabilizer 2 of FIG. 4a.

DETAILED DESCRIPTION OF THE PREFERRED EMBODIMENTS

The present invention is a stabilizer for bony structures such as the midface/maxillae and mandible for use in maxillofacial surgical procedures, and a method for use thereof.

Figures 4A, 4B:
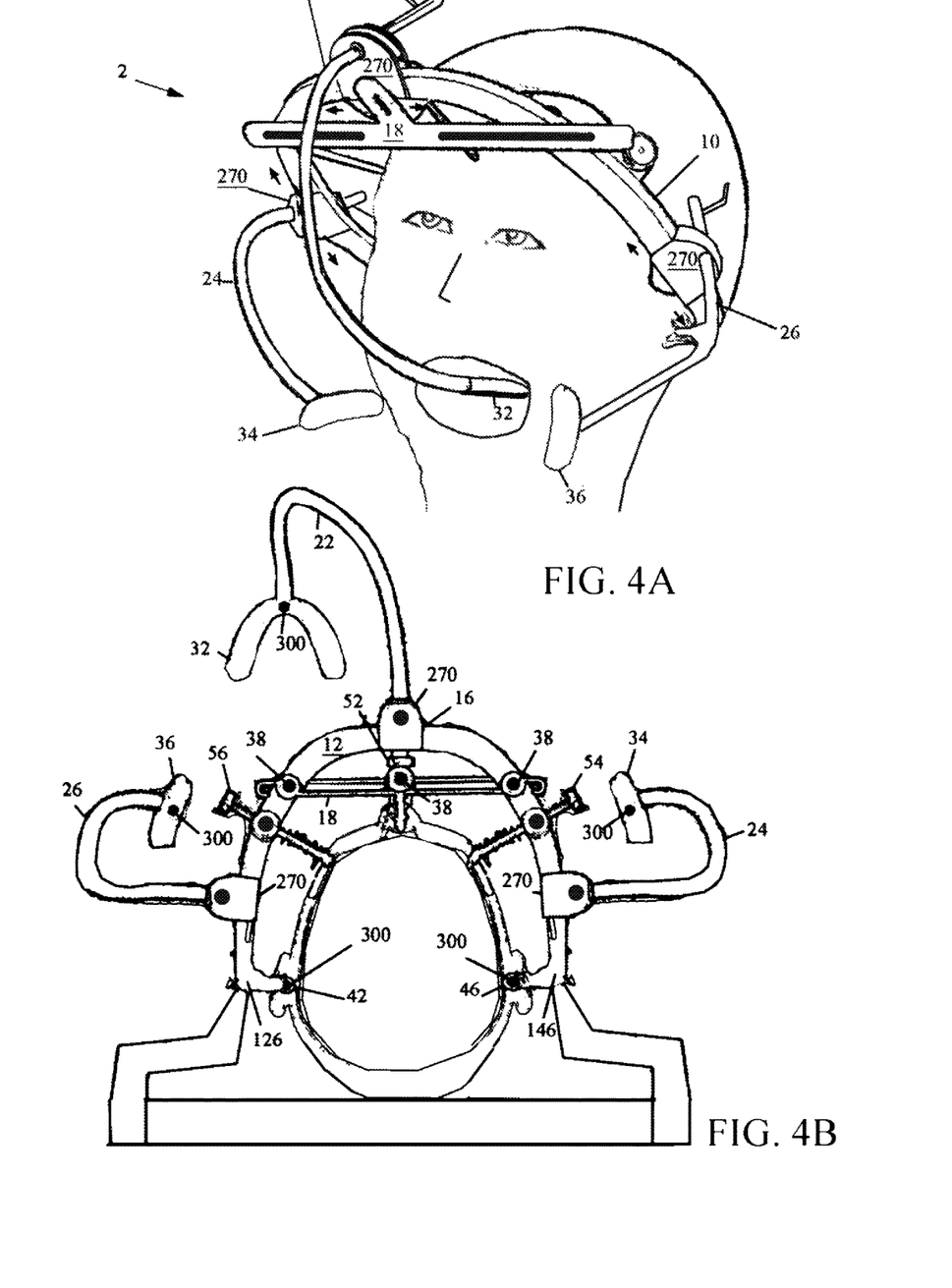

With combined reference to FIGS. 4a and 4b, the present invention is a maxillofacial surgical stabilizer 2 that is specifically adapted for positioning and stabilizing fractured or surgically mobilized bony structures such as the midface/maxillae and mandible during maxillofacial surgical procedures. Generally, stabilizer 2 comprises a light-weight rigid semi-circular head frame 10 positioned about the forefront of the patient's head, and one or more flexible locking-arms 22, 24, 26 each attached to the head frame 10 via a joint 270 that allows translation and/or adjustment relative to the head frame 10. Preferably, at least one medial arm 22 is provided and two or more optional lateral arms 24, 26 all attached to the frame 10 via corresponding joint(s) 270. The flexible locking-arms 22, 24, 26 are configured with distal receptacles to releasably hold any of a variety of instruments, implants or other accessories.

For example, as seen in FIG. 4b locking-arms 22, 24, 26 are configured with distal molds. The medial/center arm 22 is accessorized with a dental arch mold 32 that can be used to replicate the planned position and also to support, orient and stabilize the maxillae/upper jaw in relation to the skull. In the illustrated embodiment three dental molds 32, 34, 36 are held in place on the three flexible/locking arms 22, 24, 26. However, one skilled in the art will understand that arms 22-26 may be used to support other instruments, such retractor tools.

Head frame 10 is a horseshoe-shaped member comprising an elongate arcuate member 12 formed from aluminum, titanium alloy or other light weight composite material suitable for high-temperature sterilization methods. Arcuate member 12 wraps around the front of the head and a cross-piece 18 underlies the arcuate member 12 and is adjustably screwed to the frame 10 at both ends as shown, effectively bridging the frame 10 and providing a mounting for a head screw 52. The distal ends of the cross-piece 18 are screwed to the arcuate member 12 such that the cross-piece 18 forms a chord across the semi-circular forefront of the frame 10. Thumb-screws 38 are used to secure the cross-piece 18 at each end. Optional additional head screws 54, 56 may be provided as shown. In this manner, the arcuate member 12 may be adjusted to properly space it and thereby accommodate a range of acceptable head sizes, and then affix it in position by tightening thumb-screws 38 and head screws 52, 54, 56.

The heels of the arcuate member 12 likewise include inwardly directed tails 126, 146, said tails being formed as sockets for a pair of adjustable ear plugs 42, 46. Ear plugs 42, 46 are mounted on spring-biased screws to allow adjustment of the degree of distension as well as their degree of spring-biased freedom of movement. Ear plugs 42, 46 establish two fixed reference points by centering inside the patient's ear canals. Three spring-biased length-adjustable set screws 52, 54, 56 establish three additional reference points: two at the patient's temples and one above the bridge of the nose. Set screws 52, 54, 56 are adjustably threaded through collars attached to the arcuate member 12. The head of the set screws 52, 54, 55 is enlarged for finger-adjustment, and if desired a spring may be mounted on the shaft of each of the screws 52, 54, 55 to pre-bias it.

One skilled in the art should understand that some other combination of metallic pins/screws or external ear holders/plugs may suffice, so long as the ears-to-temple orientation and fixation is maintained.

Figures 5A, 5B, 5C:
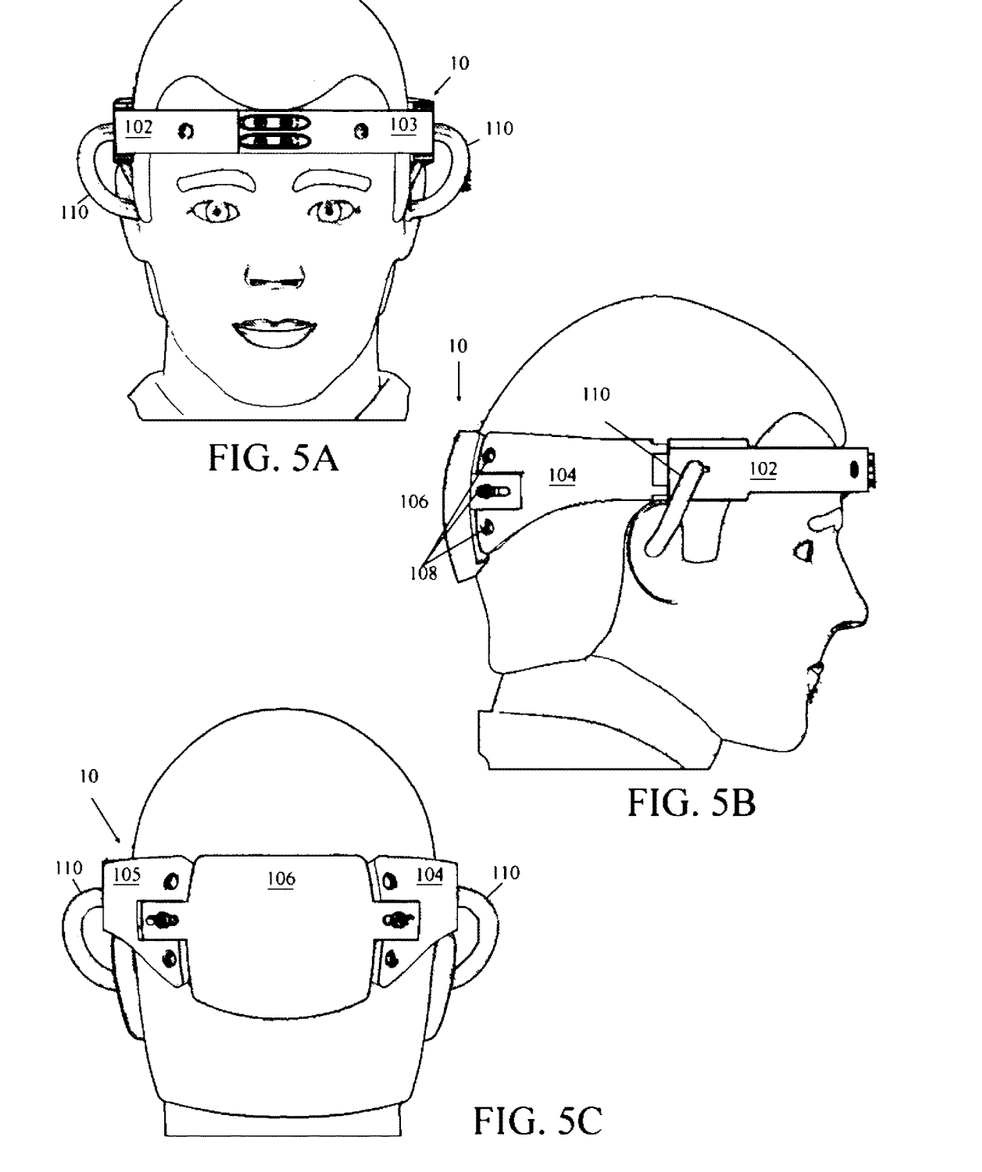
FIGS. 5a, 5b, and 5c are an anterior view, side view and posterior view of an alternative embodiment of the frame that completely encircles the patient's head.

In addition, head frame 10 can be modular. For example, FIG. 5 (A-C) illustrates an alternate embodiment of head frame 10 that is modular and adjustable. Head frame 10 is in this case constructed to encircle the patient's head completely with five (5) parts as shown in FIG. 5 (A-C). For the ease of description, these five pieces include a front right section 102, front left section 103, back right section 104, back left section 105, and the head rest section 106. The five sections 102-106 may be joined end-to-end as shown and may be configured with cooperating grooves and rails as shown to slide together with a tongue-and-groove fit. The sections 102-106 may be secured by set screw 108. Alternately, the five sections 102-106 may slide together via a ratcheting mechanism or the like. In either case the width of the head frame 10 can be adjusted to accommodate different sizes of heads through the screws 108 and the sliding/ratcheting/adjustment mechanism. As seen in FIG. 5(B) the two sections 102, 104 and 103, 105 at the sides of the frame 10 on opposing sides of the patient's head are substantially parallel. The height of the frame 10 relative to the head can be adjusted by head screws 54, 56 (as shown in FIG. 4) to accommodate different sizes of patient's heads. Ear plugs 110 can be alternatively attached to the frame 10 and arch downwardly for insertion in and stabilization against the ear orifices, thereby ensuring that the left and right sides of the head frame 10 are symmetrically placed around the patient's head. By inserting both ear plugs 110 in the patient's ears, and adjusting the distance of the ear plugs 110 to the lateral sections 102, 103 of the frame 10 to which they are attached, the patient's head can be perfectly centered between the frame's left and right sides. The center head rest section 106 also connects on both sides to the respective back right section 104 and back left section 105 via a sliding mechanism and screw(s) 108. The back right section 104 and back left section 105 are preferably bowed more in the back and turn straight on both sides. Anywhere from four to six head screws 56 may be used to secure the head frame 10 to the patient's head. Two screws are preferably positioned one on the front of the patient and at least two on the back. On each of the back right and back left sections 104, 105, two threaded holes are provided for screws 108. Typically, only two screws 108 are needed on the back side to secure the frame 10 onto the patient's skull. However, when the patient's head is large or the patient has a thick scalp additional screw holes can be used for added security. The frame 10 sits tightly against the patient's head on the back side while the front can have some space for the ease of arm attachments (not shown in FIG. 5, see FIG. 4). After the frame 10 is secured on to the patient's head, the two ear plugs 110 can be removed from the patient's ears.

Referring back to FIG. 4, the flexible locking-arms 22, 24, 26 allow for easy single handed repositioning in any direction when in an "unlocked" condition, yet maintain a secure fixed position when in a "locked" condition, and with variable user-adjustable resistance there between. All three flexible locking-arms 22, 24, 26 are identical.

Figure 6:
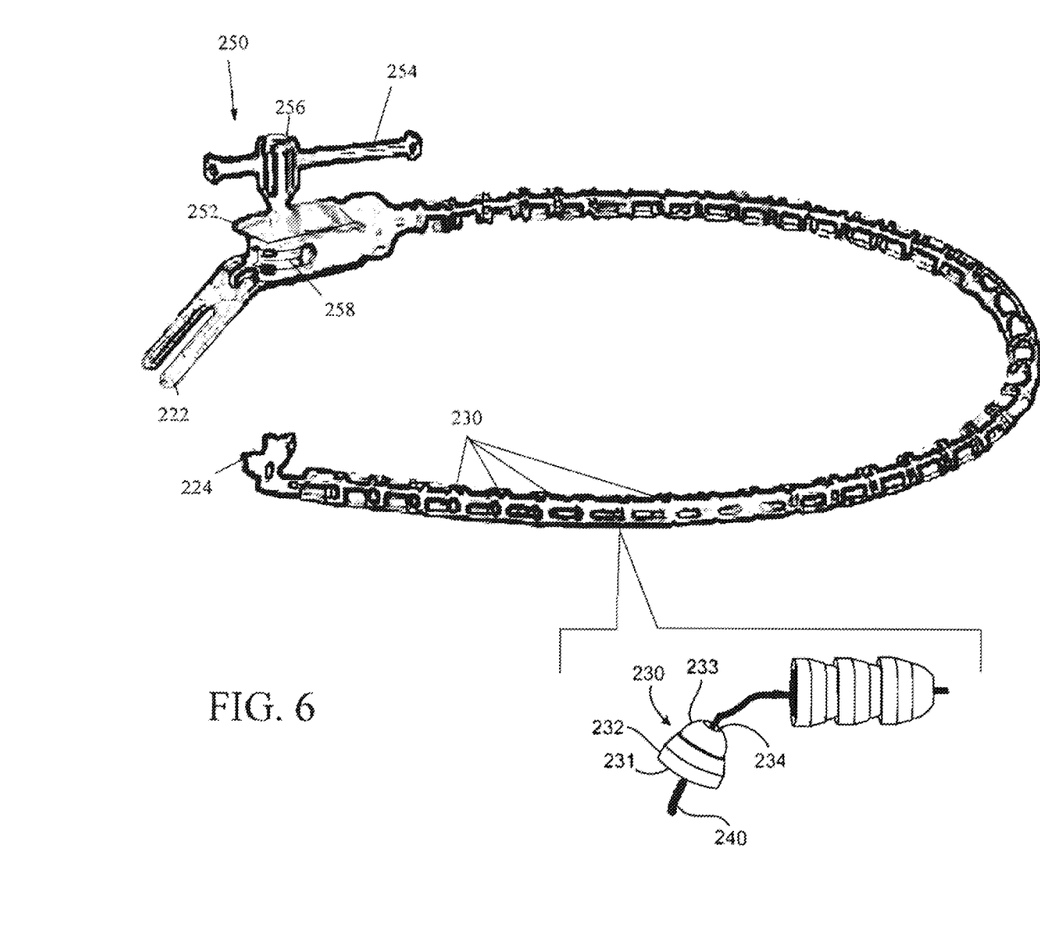
FIG. 6 is an isolated perspective view of one of the flexible locking-arms 22, 24, 26 used with the maxillofacial surgical stabilizer 2 of FIGS. 4a and 4b.

FIG. 6 illustrates a presently-preferred flexible/locking arm configuration which generally includes a yoke adapter 222 at one end for pivotal connection to the arcuate member 12, and a mounting receptacle 224 at the other end mounting a selected mouthpiece 32, 34, 36 or any other desired surgical tool that needs to be stabilized. The yoke adapter 222 is connected to the receptacle 224 by an elongate series of locking flex-joints there between. In the preferred embodiment the flex joints comprise ball-and-socket links 230 with a tensioning cable 240 anchored to receptacle 224 and running centrally through ball-and-socket links 230 to a tensioning fixture 250. Tensioning fixture 250 selectively tensions or releases ball-and-socket links 230, thereby providing an adjustable degree of flexibility of arms 22, 24, 26 ranging from limp to rigidly locked in place. Tensioning fixture 250 further comprises a rotary spindle 256 carrying a transverse handle 254. Spindle 256 is rotatably journaled into a block 252 and turns a sheave 258 carried in the block 252. An end of tensioning cable 240 is wound about the sheave 258. Thus, turning the handle 254 turns the sheave 258 and tensions or untensions cable 240. Spindle 256 is preferably ratcheted so that it cannot back up inadvertently, and may be driven by a reduction gear to improve leverage.

The tensioning cable 240 may be any suitable twisted fiber cord or cable. The cable 240 runs throughout the links 230 of the arm 22 to tensioning fixture 250, which compresses the links 230 together to increase their collective rigidity, ultimately locking them in position. There are a variety of alternative flexible arm configurations that may suffice for present purposes, the primary parameters being the ability to articulate mechanically in any direction, mechanically freeze a desired position along its entire length, and hold that position with maximum strength. The present configuration does this with ball-and-socket links 230 configured as shown in the inset to FIG. 6. A variety of different tools may be attached at the ends of the two lateral flexible/locking arms 24, 26 for pushing and pulling, such as Langeback-like retractors, partial/half/hemiarch splints, etc. The inset of FIG. 6 is an enlarged illustration of an exemplary link 230 showing geometry. Each link is a ball-and-socket design, with a convex face 233 at one end and a concave face 231 at the other end. Each convex face 233 on one link conforms to the concave face 231 on the next adjoining link, and so the ball-and-socket links 230 fit end-to-end. Each link 230 is defined by an axial passage 234 for passing the cable 240. The accuracy of the bony segments positioned and stabilized according to the procedures and with the stabilizer disclosed above can now be verified radiographically.

A computer system to aid the anthropometric analysis is also optionally provided. The computer system is referred to as the anthropometric planning system (APS). The radiographs, whether it is two dimensional or three-dimensional, can be manipulated and compared with prior radiographs in the APS. With three-dimensional computer tomography images, the bony structures can be viewed from all angles around the head, the mandible can be virtually rotated on the APS screen to reveal any gaps or obstructions, and the matching of the upper and lower teeth can also be verified. The positions of all bony segments can be fine-tuned virtually on the APS to reach their ideal position. The required translations and rotations of each of the arms to reach these ideal positions and angulations are calculated by the APS and displayed and/or printed.

The flexible/locking arms 22, 24, 26 are each connected to an adjustable joint 270 that is attached to the head frame 10 and can make translational adjustments relative to the head frame 10. The joint 270 itself also contains mechanisms to translate in transverse plane and in the sagittal plane.

Figure 10:
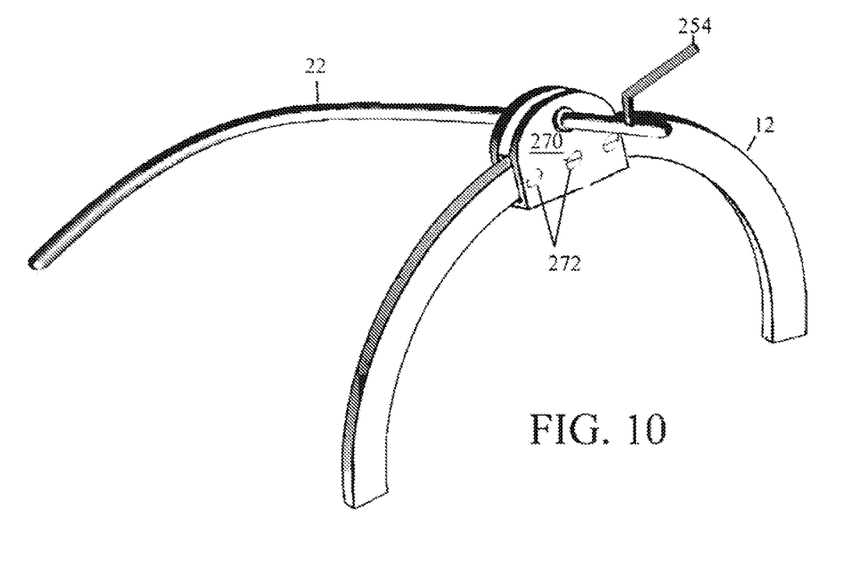
FIG. 10 is an exemplary joint 270 for attaching the flexible locking-arms 22, 24, 26 to the surgical stabilizer 2 of FIGS. 4a and 4b.

FIG. 10 is an exemplary joint 270 for attaching the flexible locking-arms 22, 24, 26 to the surgical stabilizer 2 of FIGS. 4-5. This exemplary joint 270 design has translational adjustment capability (two-way) along arcuate member 12. The arm 22 passes through joint 270 at a pivot joint (a bearing, bushing or the like) and the arm 22 can also be rotated inside the joint 270. The arm 22 can be positioned and re-positioned laterally simply by loosening one or more set screws 272.

Figure 11:
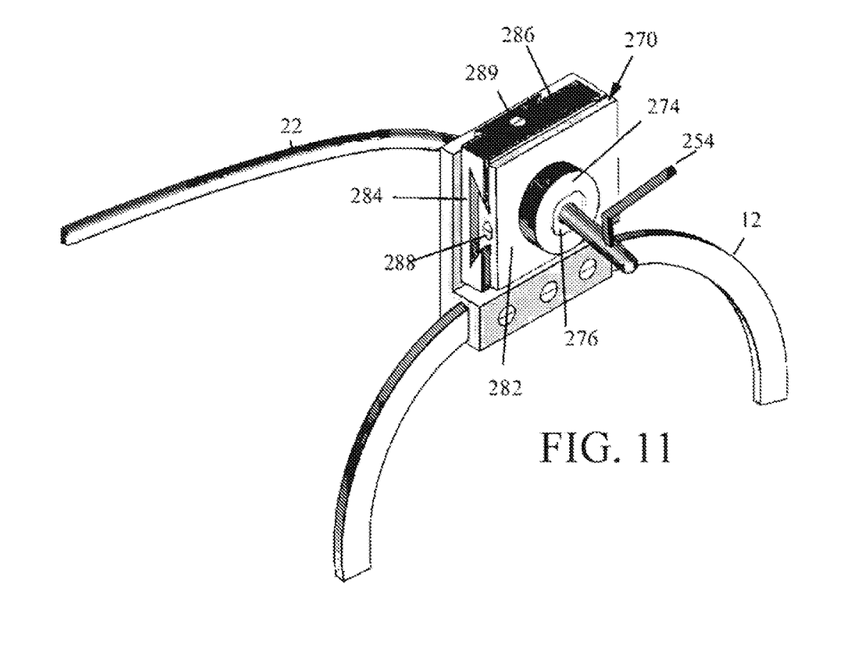
FIG. 11 is an alternate adjustable joint 275 for attaching the flexible locking-arms 22, 24, 26 to the surgical stabilizer 2 of FIGS. 4a and 4b.

FIG. 11 is an alternate adjustable joint 275 for attaching the flexible locking-arms 22, 24, 26 to the surgical stabilizer 2 of FIGS. 4-5 and providing 4-dimensional adjustment capability (three translations and one rotation). The arm 22 is secured tightly inside a rod segment 272. The rod segment 272 is positioned inside a channel in joint 270 and can slide up and down inside the channel. The rod 274 is rotatably connected to a screw 276 at the bottom. Turning the screw 276 will adjust the height of the rod 274 in the channel, which in turn moves that arm 22 in the direction of the channel. The rod 274 can also be rotated inside the channel and locked in position by a set screw (obscured). The joint 270 further comprises three brackets 282, 284, 286 joined together by orthogonal tongue and groove tracks to allow rod 274 to be moved laterally both sideways and in superior—inferior direction by turning the screw bars 288, 289 inside the top two "dove-tailed" moving plates 286, 282 to cause the plates 282, 284, 286 to slide in the desired direction. Additional adjustments in more rotational dimensions can also be implemented. The provisions of such fine adjustments of the positions of the flexible locking arms are important. They allow the surgeon to achieve perfection from a nearly perfect alignment of bony segments without loosening the stiffened locking arms and start all over.

Because a small pivot of a bony segment may require a complex combination of fine adjustments in multiple joints and in multiple dimensions of each joint, it is impractical to compute the required adjustments by hand. It is also too time consuming to make such adjustments through a trial-and-error process. Therefore, a computer system will generally be required to compute the needed fine adjustments. The availability and ranges of all forms of adjustments are known to the APS so that the APS will make executable requirements. Also, when not in use, arms 22, 24, 26 may be pushed away by releasing the tension in cable 240. By holding all the links 230 in their optimal position based on the operators' judgment, a radiological image can be obtained, and the positioning can be verified against the patient's prior images on the APS computer. The perfect bite between the upper and lower teeth can also be verified by the virtual movement based on the radiograph on the APS. If further finer adjustment is needed, the operator will first make these virtual adjustments on the APS computer, which will translate these adjustments to the actual knob-turning instructions. The surgeon can then make these fine adjustments using the adjustable joint without breaking the already stiffened arrangement. Once the positioning is verified, the surgeon can take his time to tie all the pieces together.

Figure 7:
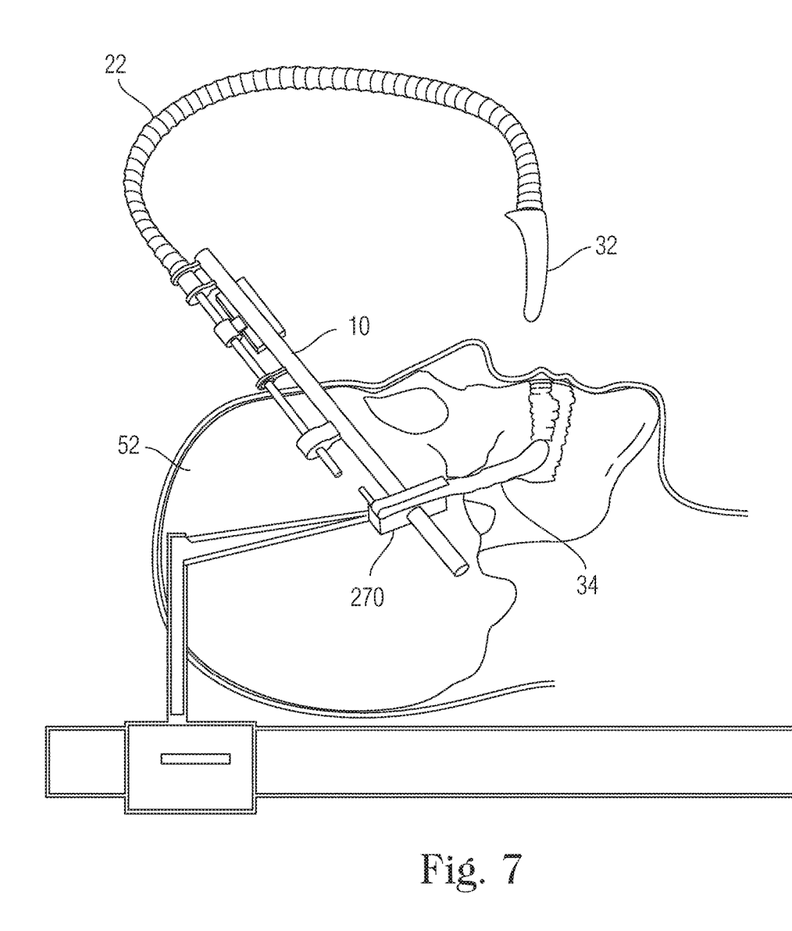
FIG. 7 is a side view of the maxillofacial surgical stabilizer 2 of FIGS. 4a and 4b illustrating its ergonomic advantages and unobtrusive presence from a surgeon's perspective.

FIG. 7 is a side perspective view illustrating the geometry of the maxillofacial surgical stabilizer 2 according to the present invention, with head frame 10 attached to the patient's supporting platform/operating bed to provide immobilization of the patient's head relative to the patient support platform/operating bed if such immobilization is desired. The combination of pins/screws, one above the nose bridge and two at the temple, plus ear-plugs, orients the flat head frame 10 along an ears-to-temple orientation which is least obtrusive during maxillofacial surgery. The device may provide:

Support for the bony segments;
Retraction of soft tissues (fornix exposure);
Positioning of the segments;
Stabilization of the segments while fixating it.

Also provided is a method for accurately orienting and positioning mobile bony fragments using the maxillofacial surgical stabilizer 2 according to the present invention, to thereby stabilize them prior to fixation with hardware such as metal plates and screws.

Figure 8:
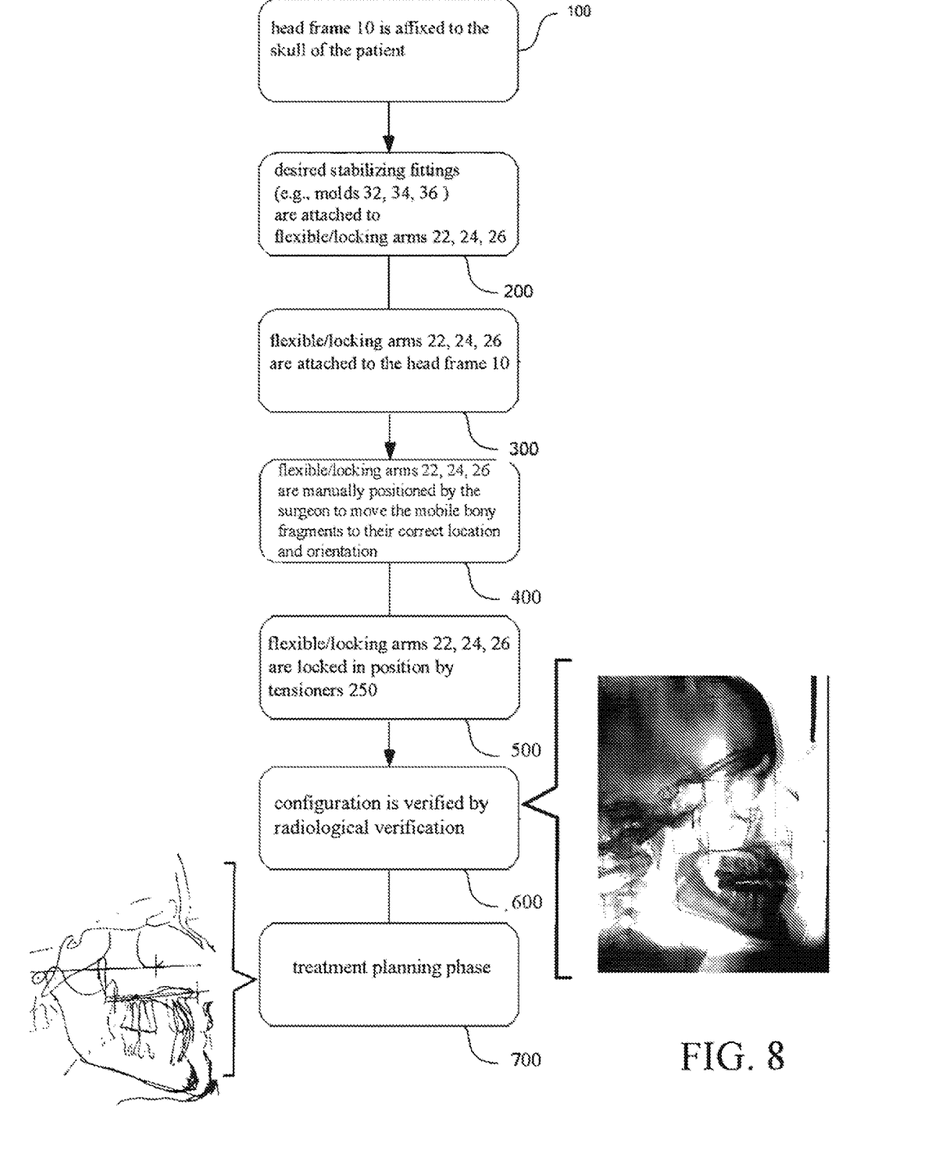
FIG. 8 is a block diagram illustrating the steps involved in using the maxillofacial surgical stabilizer 2 of FIGS. 4a and 4b according to the method of the present invention.

FIG. 8 is a block diagram illustrating the steps involved in using the maxillofacial surgical stabilizer 2 of FIGS. 4-5 according to the method of the present invention.

At step 100 the head frame 10 is affixed to the skull of the patient by positioning the head frame 10 (fully or partially surrounding the head of the patient) at an angle running from ears to temple, and fixating by screws 52, 54, 56 and ear plugs 42, 46.

At step 200 the desired stabilizing fittings such as dental molds 32, 34, 36 are attached distally to the receptacles at the ends of the flexible/locking arms 22, 24, 26.

At step 300 flexible/locking arms 22, 24, 26 are attached to the head frame 10.

At step 400 flexible/locking arms 22, 24, 26 are manually positioned by the surgeon to move the mobile bony fragments to their correct location and orientation.

At step 500 with mobile bony fragments to their correct location and orientation, the flexible/locking arms 22, 24, 26 are locked in position by tensioners 250. Thereby the mobile bony fragments are stabilized at their desired locations with the correct orientation.

At step 600 with mobile bony fragments stabilized in their correct location and orientation by flexible/locking arms 22, 24, 26, the configuration is verified by radiological verification before all bony segments are fixated with metallic hardware. This, for example, may entail an X-ray, ultrasound, or computed tomography (CT) scan, or as seen in the inset, magnetic resonance imaging (MRI) to provide a planning image (see inset).

At step 700 a treatment planning phase is implemented using image processing software in which reference indicia and bony segments are identified on the image file to optimize alignment, and the accuracy of the imaged alignment is verified (arms 22, 24, 26 repositioned as needed). For example, the surgeon may verify position prior to fixation of both skeletal segments and hardware in respect to a planned 3D orientation of upper and lower dental arches in a preformed surgical wafer in the occlusal plane. This step 700 may entail automated identification and translation of pixel image data into 3D stereolithographic cadcam models. If desired, the treatment planning step 700 may entail comparison of the radiographs of the patient taken prior to the traumatic injury or operation.

In a preferred embodiment treatment planning is carried out using an automated anthropometric planning system (APS). Given the fact that there may be multiple joints/adjustment screws 52, 54, 56, 250, each with multiple degrees of freedom, there are myriad possible adjustments for achieving an optimum fit. It is not feasible for an operator to figure out how to adjust the knobs/screws/joints screws 52, 54, 56, 250 to create a perfect fit by trial-and-error. Therefore, it is preferable to optimize the fit using computer optimization. For this purpose the maxillofacial surgical stabilizer 2 is provided with a plurality of radiation-opaque markers 300 at predetermined locations. For example, as shown in FIG. 5, five (5) radiographic markers 300 are shown. Markers 300 appear as dark spots in radiographic images, and the known relative spatial coordinates of the five markings may be used to adjust and optimize the accuracy of the bony segments positioned and stabilized with the stabilizer 2, and such positions can be verified radiographically.

Figure 9:
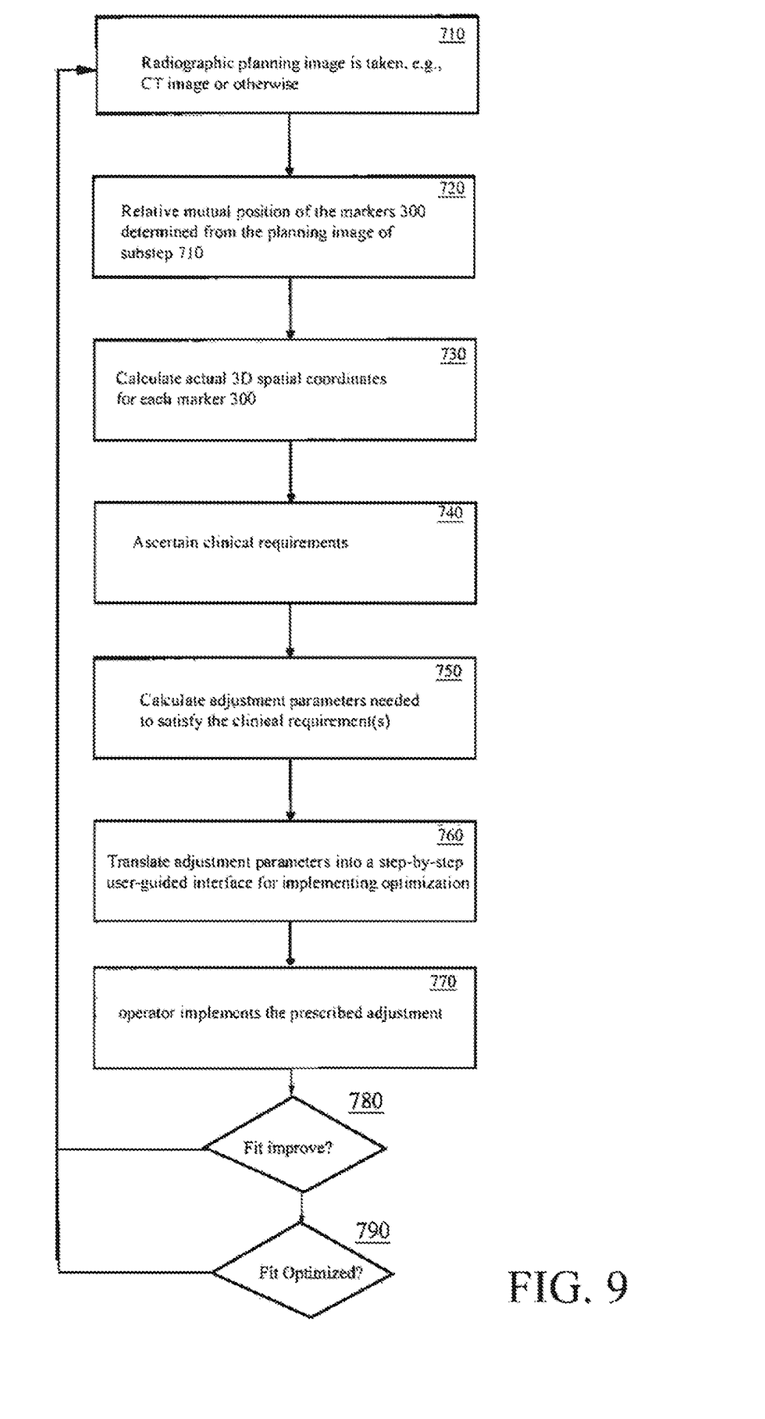
FIG. 9 is a flowchart illustrating the detailed substeps of the treatment planning phase of FIG. 8.

Reference is now made to FIG. 9, which is a flowchart illustrating the detailed substeps of the treatment planning phase of FIG. 8, with reference to the anthropometric planning system (APS) of the present invention.

At step 710 with the maxillofacial surgical stabilizer 2 applied to a patient a planning image is taken, such as a CT image.

At step 720 the relative mutual position of the markers 300 are determined from the planning image. Identification of the markers 300 and their locations may be carried out automatically, for example using conventional marker location software using suitable marker-locating algorithms.

At step 730, on the basis of the relative mutual position of the markers 300 it is possible to calculate the actual spatial coordinates for each marker 300 ($x_n$, $y_n$, $z_n$). The spatial coordinates of markers 300 correspond to anatomical features (e.g., jaw alignment, bone segment placement, etc.) and/or surgical tool placement (e.g., mold placement). Step 730 may be performed by a conventional imaging workstation and the identified markers and relative position data may be transferred (automatically or manually) to a treatment planning workstation for subsequent steps.

At Step 740 one or more clinical requirements are determined. The clinical requirement (s) may be preset by a user. For example, the user may be provided with jaw positioning options (e.g., through a user interface), to set clinical parameters for the treatment, including any tolerance threshold limits. The user may be guided/restricted in the placement options and/or range of values selectable as a threshold. For example, the user may be presented with user interface including a 3D model of the jaw and selection controls for selecting an optimum position and tolerance threshold values from a predefined range of values. Of course, some clinical requirement(s) may be predefined and stored in the system, and any clinical requirement that is not specified by the user may be assigned a predefined default value.

At Step 750 one or more adjustment parameters are calculated as needed to satisfy the clinical requirement(s) based on the spatial coordinates of markers 300. Calculation of the adjustment parameter(s) may include determining one or more optimization parameter(s) for optimum placement of anatomical features (e.g., jaw alignment, bone segment placement, etc.) and/or surgical tool placement (e.g., mold placement. The adjustment parameters are calculated using a predefined empirical rule/relationship, or optimization algorithm. Because there is only one perfect fit, a simple "greedy search" algorithm can be used. A greedy algorithm is an algorithm that follows the problem solving heuristic of making the locally optimal choice at each step with the hope of finding an optimum solution. For example, an adjustment parameter may be quantified by the lack of a gap width between two bony segments or between the upper and lower teeth. The calculated adjustment parameter will reflect a degree of adjustment necessary to interpose a proper gap width between the two bony segments/teeth.

At step 760, the adjustment parameters are automatically translated by the treatment planning workstation into a step-by-step user-guided interface for implementing the optimization process. Again, there are myriad possible adjustments and it is not practical for an operator to figure out how to adjust the knobs/screws/joints screws 52, 54, 56, 250 by trial-and-error, nor for the treatment planning workstation to calculate one perfect adjustment. Therefore, the treatment planning system must rely on computer optimization. At step 760 the step-by-step user-guided interface may suggest one or more initial adjustments to begin implementing the optimization process. The optimization algorithm may randomly select a knob to turn along a randomly chosen direction by a random number of degrees, optionally multiplied by an exponential function of the number of adjustment tries. The exponential function is sometimes referred to as the "cooling speed", it ensures convergence (that the adjustments get smaller) as the number of trials increases. One skilled in the art will understand that other optimization algorithms, such as genetic algorithms or gradient-descent; can also be used for finding the adjustments needed to achieve a perfect fit.

At step 770 the operator implements the prescribed adjustment, and a second planning image is taken.

At step 780 if the stabilizer 2 fit improves, the system will accept the adjustment. If the fit is worse the optimizer will not accept the adjustment.

At step 790 if the stabilizer 2 fit is fully optimized the system ends the optimization procedure.

The above-described method improves clinical performance by facilitating surgical planning and implementation. The presence of the device 2 does not interfere with the maneuvering of the surgeons or with anesthesia equipment because the frame remains away from the area of interest. The device and method also provide the ergonomic comfort for the assisting nurses and residents. Indeed, from an educational stand point the method and device of the invention provides an unobstructed panoramic view to assisting residents to view and assist in the procedure. Thus the device can be used to implement teaching strategies, thereby improving education.

Therefore, having now fully set forth the preferred embodiment and certain modifications of the concept underlying the present invention, various other embodiments as well as certain variations and modifications of the embodiments herein shown and described will obviously occur to those skilled in the art upon becoming familiar with said underlying concept. It is to be understood, therefore, that the invention may be practiced otherwise than as specifically set forth in the appended claims.

What is claimed is:

1. A maxilla/cranial-facial surgical stabilizer for use during maxilla/cranial-facial surgery, comprising:
   a metal frame configured to be fixated to a skull of a patient to establish a fixed frame of reference there about;
   at least three flexible arms each attached at one end to said frame and protruding from said frame to a distal end, each of said flexible arms having a fully flexible state of omnidirectional flexibility along its entire length for bending to a desired orientation a rigid state along its entire length, and a locking mechanism for locking said flexible arm in said rigid state at a desired orientation, and a mounting receptacle at the distal end of each of said flexible arms configured for removable attachment of one of the maxillofacial surgical aids, such as, a dental arch mold or template, a clamp, a holder or a tissue retractor;
   whereby said maxilla/cranial-facial surgical stabilizer may be fixated to a skull of a patient and each of said arms bent to and locked in a desired orientation relative to said fixed frame of reference to allow the said maxillofacial surgical aids to support, orient and stabilize the bony structures and/or segments thereof, relative to said skull of said patient.

2. The maxilla/cranial-facial surgical stabilizer according to claim 1, further comprising a dental arch mold attached to the mourning receptacle at the distal end of one of said flexible arms to support, orient and stabilize a patient's maxillae/upper jaw in relation to said patient's skull.

3. The maxilla/cranial-facial surgical stabilizer according to claim 1, wherein said flexible arm is attached to said frame by a joint.

4. The maxilla/cranial-facial surgical stabilizer according to claim 3, wherein said joint is translationally adjustable about said frame.

5. The maxilla/cranial-facial surgical stabilizer according to claim 1, further comprising a medial arm and two lateral arms.

6. The maxilla/cranial-facial surgical stabilizer according to claim 1, further comprising a dental clamp attached to the mourning receptacle at the distal end of one of the medial arms to place both upper and lower jaw in correct occlusion.

7. The maxilla/cranial-facial surgical stabilizer according to claim 1, wherein the locking mechanism comprises a tightening lever for continuously increasing stiffness of said flexible arm.

8. The maxilla/cranial-facial surgical stabilizer according to claim 1, wherein said flexible arm comprises a plurality of ball-and-socket links.

9. The maxilla/cranial-facial surgical stabilizer according to claim 1, wherein said head frame is substantially horseshoe-shaped.

10. The maxilla/cranial-facial surgical stabilizer according to claim 1, wherein said head frame comprises a plurality of sections slidably attached together.

11. A maxilla/cranial-facial surgical stabilizer for use during maxilla/cranial-facial surgery, comprising:
   a head frame formed as a rigid ring at least partially encircling a patient's head to establish a fixed frame of reference there about;
   at least three flexible locking arms, each said flexible locking arm further comprising
      an adjustable base joint at one end configured for releasable attachment to said head frame,
      a mounting socket at another end for releasable attachment of a surgical device chosen from among the group of a dental arch mold or template, a holder and a tissue retractor,
      a flexible arm extending between said base joint and said mounting socket formed of a plurality of flexible locking joints and having a fully flexible state of omnidirectional flexibility along its entire length for bending to a desired orientation, and a rigid state along its entire length, and
      a tensioner mounted on said flexible arm for adjusting tension of said flexible arm along said plurality of flexible locking joints and locking said flexible arm in said rigid state at a desired orientation; and
      one of a dental mold, clamp, holder or tissue retractor attached to the mounting socket of each flexible locking arm.

12. The maxilla/cranial-facial surgical stabilizer according to claim 11, wherein said adjustable joint is translationally adjustable relative to the said frame, thereby allowing adjustment of the corresponding arm while in the rigid state.

13. The maxilla/cranial-facial surgical stabilizer according to claim 11, further comprising a dental arch mold attached to the mounting receptacle at the distal end of one of said flexible arms to support, orient and stabilize a patient's maxillae/upper jaw in relation to said patient's skull.

14. The maxilla/cranial-facial surgical stabilizer according to claim 11, wherein flexibility of said flexible arm is continuously user-variable.

15. The maxilla/cranial-facial surgical stabilizer according to claim 13, wherein said flexible arm comprises a plurality of ball-and-socket links.

* * * * *